(12) United States Patent
Singh et al.

(10) Patent No.: US 11,432,867 B2
(45) Date of Patent: *Sep. 6, 2022

(54) MARGIN EXTENSION DEVICE AND METHOD

(71) Applicant: City of Hope, Duarte, CA (US)

(72) Inventors: Gagandeep Singh, Duarte, CA (US);
Jonathan Kessler, Duarte, CA (US)

(73) Assignee: City of Hope, Duarte, CA (US)

( * ) Notice: Subject to any disclaimer, the term of this patent is extended or adjusted under 35 U.S.C. 154(b) by 300 days.

This patent is subject to a terminal disclaimer.

(21) Appl. No.: 16/531,557

(22) Filed: Aug. 5, 2019

(65) Prior Publication Data

US 2019/0350641 A1 Nov. 21, 2019

Related U.S. Application Data

(62) Division of application No. 14/877,261, filed on Oct. 7, 2015, now Pat. No. 10,368,938.

(60) Provisional application No. 62/061,021, filed on Oct. 7, 2014.

(51) Int. Cl.
| | |
|---|---|
| *A61B 18/12* | (2006.01) |
| *A61B 18/14* | (2006.01) |
| *A61N 1/32* | (2006.01) |
| *A61B 18/00* | (2006.01) |

(52) U.S. Cl.
CPC .... *A61B 18/1402* (2013.01); *A61B 2018/005* (2013.01); *A61B 2018/00077* (2013.01); *A61B 2018/00327* (2013.01); *A61B 2018/00488* (2013.01); *A61B 2018/00494* (2013.01); *A61B 2018/00541* (2013.01); *A61B 2018/00559* (2013.01); *A61B 2018/00577* (2013.01); *A61B 2018/00613* (2013.01); *A61B 2018/143* (2013.01); *A61B 2018/1467* (2013.01); *A61N 1/327* (2013.01)

(58) Field of Classification Search
CPC ...... A61B 18/1402; A61B 2018/00541; A61B 2018/00577; A61B 2018/143; A61B 2018/1467
See application file for complete search history.

(56) References Cited

U.S. PATENT DOCUMENTS

| | | | |
|---|---|---|---|
| 6,056,747 A * | 5/2000 | Saadat | A61B 18/14 606/42 |
| 2003/0084907 A1 | 5/2003 | Pacek et al. | |
| 2003/0125640 A1 | 7/2003 | Klimberg et al. | |
| 2003/0130711 A1* | 7/2003 | Pearson | A61B 18/1477 607/101 |
| 2005/0000525 A1 | 1/2005 | Klimberg et al. | |

(Continued)

*Primary Examiner* — Daniel W Fowler
(74) *Attorney, Agent, or Firm* — Mintz Levin Cohn Ferris Glovsky and Popeo, P.C.

(57) ABSTRACT

A margin extension device and method are disclosed herein. The margin extension device can be used for ablating one or several cancer cells and can include a contact member and a plurality of electrodes. The contact member can be electrically conductive, and can electrically connect the electrodes. The margin extension device can further include one or several leads that connect the electrodes of the margin extension device to a treatment controller. The treatment controller can include a pulse generator that can generate one or several electrical pulses that generate one or several electrical fields in tissue proximate to the margin extension device.

29 Claims, 9 Drawing Sheets

(56) References Cited

U.S. PATENT DOCUMENTS

| | | |
|---|---|---|
| 2008/0200912 A1 | 8/2008 | Long |
| 2008/0214986 A1 | 9/2008 | Ivorra et al. |
| 2010/0030211 A1* | 2/2010 | Davalos ................ C12N 13/00 606/41 |
| 2010/0179530 A1 | 7/2010 | Long et al. |

* cited by examiner

MARGIN EXTENSION DEVICE AND METHOD

REFERENCE RELATED APPLICATIONS

This application is a divisional of U.S. application Ser. No. 14/877,261 filed on Oct. 7, 2015, issuing on Aug. 6, 2019 as U.S. Pat. No. 10,368,938 and claims priority to U.S. Provisional Application Ser. No. 62/061,021 entitled "Margin Extension Device and Method" and filed on Oct. 7, 2014. The disclosures are hereby incorporated by reference in their entireties.

BACKGROUND

Cancer is a group of diseases involving abnormal cell growth with the potential to invade or spread to other parts of the body. In some cases, a patient with cancer may develop one or more tumors that can be located in different portions of the body. In some instances, the best treatment for cancerous tumors is to surgically excise the tumor via a surgery, or to kill the cancerous cells forming the tumor via, for example, radiation or electroporation. In the case in which a tumor is surgically excised, best practices call for the excision of an amount of tissue surrounding the tumor, which tissue is referred to herein as a surgical margin. The surgical margin is removed as cancerous cells may be outside of the tumor, and thus only excising the tumor would not remove such cells.

While these techniques have proven effective, they are limited in their applicability, especially when the tumor is proximate to one or several critical structures such as, for example, a critical organ, an artery including a systemic artery, or the like. In such a situation, a surgeon may be unable to remove an adequate surgical margin to most effectively eliminate the cancerous cells and/or to hinder the spread of the cancer. Thus, further methods, systems, and devices are required to provide more complete treatment of cancer.

SUMMARY

One aspect of the present disclosure relates to a surgical margin extender. The margin extender includes an anode, a cathode, and a contact member. In some embodiments, the contact member is a conductive material, and the contact member electrically connects the anode and the cathode. In some embodiments, the contact member electrically connects the anode and cathode at a distance such that the anode and the cathode can electroporate a cancer cell.

In some embodiments, the anode can be a first elongate member and the cathode can be a second elongate member. In some embodiments, the first elongate member can be a first needle having a first proximal end and a first distal end, and the second elongate member can be a second needle having a second proximal end and a second distal end. In some embodiments, the first elongate member and the second elongate member are parallel when connected to the contact member. In some embodiments, the first elongate member can have a first voltage-delivery portion and a first insulative portion, and the second elongate member can have a second voltage-delivery portion and a second insulative portion.

In some embodiments, the first and second voltage-delivery portions of the first and second elongate members are at least partially connected to the contact member. In some embodiments, the first and second voltage-delivery portions of the first and second elongate members are completely connected to the contact member. In some embodiments, the contact member has a contact surface configured for connecting with a living tissue. In some embodiments, the first and second voltage-delivery portions of the first and second elongate members extend from within the contact member to beyond the contact surface of the contact member.

In some embodiments, the contact member is rigid, and in some embodiments, the contact member is flexible. In some embodiments, the margin extender includes a handle extending from the contact member, which handle can allow gripping of the treatment device.

One aspect of the present disclosure relates to a treatment system. The treatment system includes a control module that generates at least one electrical pulse. In some embodiments, the electrical pulse can be created so as to allow the electroporation of a cancer cell by the electrical pulse. The treatment system can include a margin extender having an anode, a cathode, and a contact member electrically connecting the anode and cathode in a configuration such that the anode and the cathode can electroporate the cancer cell via the transmission of the at least one pulse to a living tissue. The margin extender can include leads connecting the anode and the cathode to the control module.

In some embodiments, the anode is a first elongate member and the cathode is a second elongate member. In some embodiments, the first elongate member and the second elongate member are parallel when connected to the contact member. In some embodiments, the contact member can have a contact surface that is able to electrically connect with a living tissue.

In some embodiments, the first and second elongate members are parallel with the contact surface. In some embodiments, the first and second elongate members intersect the contact surface. In some embodiments, one or both of the first and second elongate members extend from one side of the contact surface to the other side of the contact surface. In some embodiments, the contact member is rigid, and in some embodiments, the contact member is flexible. In some embodiments, the treatment system can include a handle extending from the contact member, which handle can allow gripping of the treatment.

One aspect of the present disclosure relates to a method of generating a negative margin around an excised tumor. The method includes excising a tumor from a living tissue, which excision of the tumor does not create a negative margin at a portion of the tissue surrounding the tumor, applying a margin extender to the portion of the tissue surrounding the tumor that does not have a negative margin. In some embodiments, the margin extender can include: an anode, a cathode, and a contact member. In some embodiments, the contact member is a conductive material that electrically connects the anode and the cathode; and the contact member electrically connects the anode and cathode at a distance such that the anode and the cathode can electroporate a cancer cell. In some embodiments, the method includes applying an electrical current to the contact member via the anode and cathode, which application of the electrical current to the contact member via the anode and the cathode electroporates the cancer cell in the portion of the tissue to which the margin extender is applied.

In some embodiments, applying the margin extender to the portion of the tissue surrounding the tumor that does not have a negative margin includes wrapping the margin extender at least partially around tissue. In some embodiments, applying the margin extender to the portion of the tissue surrounding the tumor that does not have a negative margin includes at least partially filling a void left by the excised tumor with the margin extender. In some embodiments, filling the void left by the excised tumor with the margin extender includes: inserting the anode and the cathode into the void, and connecting the anode and cathode with the contact member.

In some embodiments, the anode and cathode are inserted into the void after being connected by the contact member. In some embodiments, the anode and cathode are connected by the contact member after being inserted into the void.

One aspect of the present disclosure relates to a method of treating a cancer. The method includes: identifying the location for providing a treatment, and applying a margin extender to tissue at the treatment location. In some embodiments, the margin extender includes: an anode, a cathode, and a contact member. In some embodiments, the contact member is and/or includes a conductive material that electrically connects the anode and the cathode; and which contact member electrically connects the anode and cathode at a distance such that the anode and the cathode can electroporate the cancer cell. In some embodiments, the method can include applying an electrical current to the contact member via the anode and cathode. In some embodiments, the application of the electrical current to the contact member via the anode and the cathode electroporates a cancer cell at the treatment location.

In some embodiments, the tissue proximate to the cancer cell can be located on an exterior portion of the body, and in some embodiments, the tissue proximate to the cancer cell can be located on an interior portion of the body. In some embodiments, the interior portion of the body is accessible via an existing orifice. In some embodiments, the interior portion of the body comprises at least one of: a nasal passageway, a mouth, a throat, an esophagus, a trachea, a vagina, a rectum, and a colon.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Definitions

As used herein, a "cancer" is a group of diseases involving abnormal cell growth with the potential to invade or spread to other parts of the body. Cancer can be manifest in one or several cancer cells, also referred to herein as "cancerous cells." These cancer cells can be scattered through all or a portion of a living body such as a living human body, or some or all of these cancer cells can aggregate together to form a tumor. A "tumor" as referred to herein is an abnormal growth of body tissue that can be cancerous, also referred to herein as "malignant," or non-cancerous, also referred to herein as "benign." As used herein, "tissue" refers to an aggregate of cells that can include or exclude the intercellular material of the aggregate of cells. These cells can be of the same or of a different kind.

A "surgical procedure" as used herein means a medical procedure in which a treatment is delivered to a portion of a living body such as a living human body. This procedure can be performed on an internal portion of the living body, or on an external portion of the human body. When the procedure is performed on an internal portion of the hying body, the internal portion of the living body can be accessed via a natural opening, also referred to herein as an "orifice," in the living body, or via an opening created in the living body such as, for example, an incision created with one or several instruments. A "treatment" as used herein is provided during the medical procedure and can be performed to diagnose a condition, ailment, or disease and/or repair damage or arrest disease in the living body. The treatment can include, for example, excision of one or several cells, tissues, and/or organs; connection of one or several cells, tissues, and/or organs; separation of one or several cells, tissues, and/or organs; ablation of one or several cells, tissues, and/or organs; electroporation of one or several cells, tissues, and/or organs; and/or implantation of an object such as one or several cells, tissues, and/or organs, a medical device, or a medication.

As used herein, "excision" refers to the act or procedure of removing by cutting out. When a tumor is excised, tissue forming a surgical margin may also be excised. As used herein, a "surgical margin," also referred to herein as a margin, is visibly normal/healthy tissue around a cell, tumor, growth, and/or malignancy that is removed during the excision of the cell, tumor, growth, and/or malignancy. The margin can be a negative margin, a close margin, or a positive margin. As used herein, a "negative margin," also referred to as a clear or clean margin, describes the circumstance in which no cancer cells are identified at the outer edge of the excised tissue. In many circumstances, a negative margin is identified when no cancer cells are closer than approximately 1 cm, 0.5 cm, 0.2 cm, 0.1 cm, or any other or intermediate distance from the outer edge of the excised tissue. As used herein, a "close margin" identifies the circumstance in which cancer cells are identified close to the outer edge of the excised tissue. In some circumstances, a close margin is identified when cancer cells are closer to the outer edge of the excised tissue than approximately 1 cm, 0.5 cm, 0.2 cm, 0.1 cm, or any other or intermediate distance. As used herein, a "positive margin" identifies the circumstance in which cancer cells are identified at the outer edge of the excised tissue. Significantly, treatment outcomes are progressively more positive as the margin increases from a positive margin, to a close margin, and to a negative margin. Thus, in many circumstances, additional surgery and/or treatment may be prescribed when a positive or close margin is identified.

As used herein, "electroporation" describes an increase in the electrical conductivity and permeability of the cell plasma membrane caused by the application of an electrical field. The electroporation can be reversible or irreversible. As used herein, "irreversible electroporation" (IRE) is a soft tissue ablation technique using electrical fields, which can be short but strong, to create permanent nanopores in the cell membrane, to thereby disrupt the cellular homeostasis. These permanent nanopores can result in cellular death. The resulting cell death results from apoptosis and not necrosis as in all other thermal or radiation based ablation techniques.

As used herein, an "electrode" is an electrical conductor that can be one or both of an anode and a cathode. As used herein, an "anode" is an electrode through which positive electric charge flows into an electrical device, and a "cathode" is the electrode from which a current leaves an electrical device. In some embodiments, the electrodes can be replaced with one or several probes such as, for example, one or several radio-frequency ablation (RFA) probes, one or several microwave probes, or the like.

"Approximately" as used herein refers to 20%, 10%, 5%, or 1% of an identified value or of an identified range.

Treatment Systems

Figure 1:
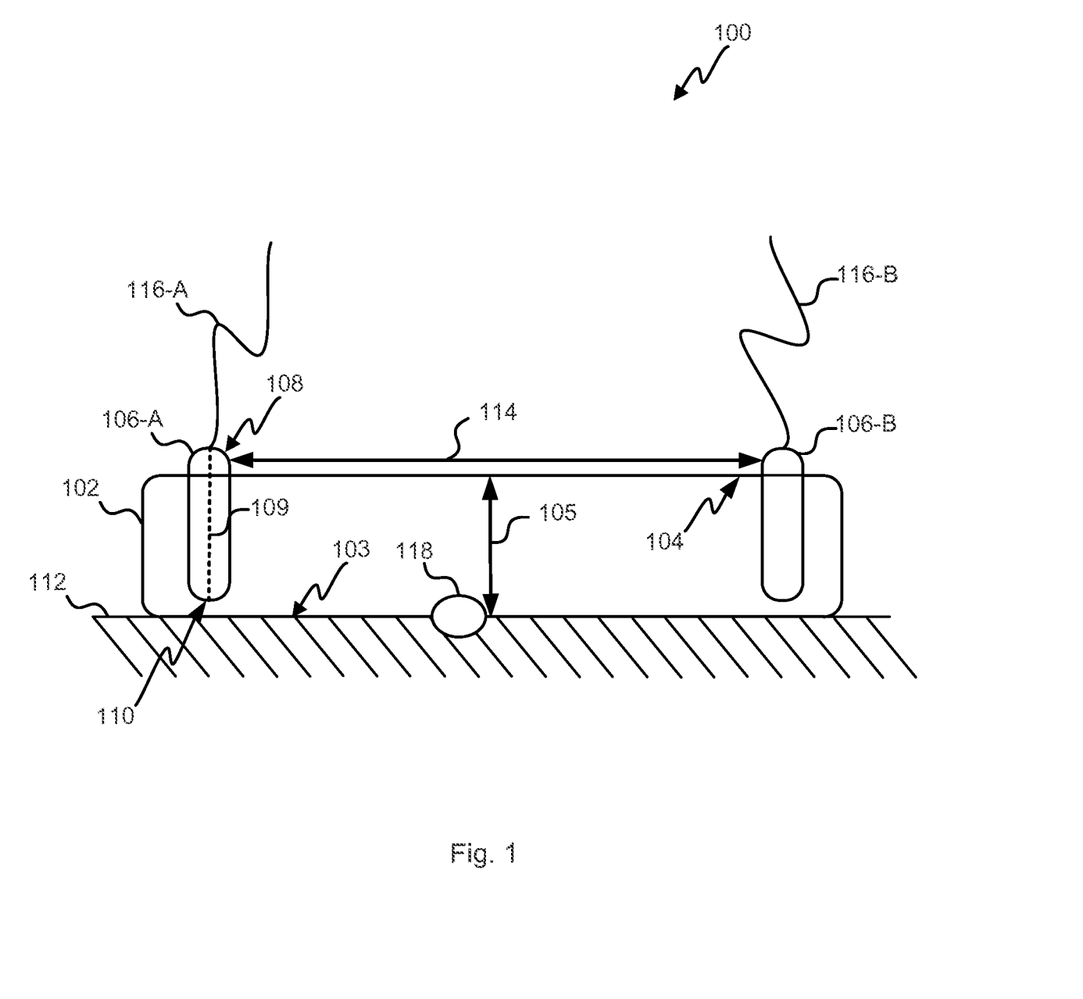
FIG. 1 is a front view of one embodiment of a treatment device.

With reference to FIG. 1, a front view of one embodiment of a treatment device 100, also referred to herein as a margin extension device and/or an ablation device, is shown. The treatment device 100 can be configured for applying to and/or placing proximate to a portion of a living body, which portion can be an internal or an external portion, and generating an electrical field in that portion of the living body. The treatment device 100 can be used as a stand-alone treatment, or can be used in connection with other treatments. Specifically, in some embodiments in which one or several cancer cells are accessible without the creation of an incision, the treatment device 100 can be the sole source of treatment for the one or several cancer cells, and in other embodiments, the treatment device 100 can be used in connection with another treatment such as, for example, the excision of one or several cancer cells or tumors. In such an embodiment, the treatment device 100 can be used to improve the surgical outcome of the excision by either generally or selectively increasing the surgical margin by ablating one or several cancer cells proximate to the treatment device.

The treatment device 100 can include a contact member 102. The contact member 102 can be configured to hold electrodes 106, including anode 106-A and cathode 106-B, and to contact tissue 112 of the living body. The contact member 102 can be a variety of shapes and sizes. In some embodiments, the shapes and sizes of the contact member 102 are limited by the desired use of the contact member 102; thus, when it is desired to use the contact member 102 to ablate one or several cancer cells in a small piece of tissue, the contact member 102 may be smaller, and when it is desired to use the contact member 102 to ablate one or several cancer cells in a large piece of tissue, the contact member 102 may be larger.

In some embodiments, the electrodes 106 can include different portions having different functions at different locations of the electrodes 106. These regions can include, for example, a voltage-delivery portion that can be a conductive portion, and an insulative portion. In some embodiments, a single electrode 106 may have multiple voltage-delivery portions separated by one or several insulative portions. In such an embodiment, a single electrode may include both an anode 106-A and a cathode 106-B. In such embodiments in which the electrodes 106 have one or several voltage delivery portions, some, none, or all of the voltage delivery portions can be both physically and electrically connected to the contact member 102.

The contact member 102 can be made from a variety of materials. In some embodiments, the contact member 102 can be conductive, and particularly, can be conductive and biocompatible. In some embodiments, the contact member 102 can be a conductor, and in some embodiments, the contact member 102 can comprise an ionic material and/or electrolyte. In some embodiments, the conductivity of the contact member 102 can be configured to match and/or correspond with the conductivity of the tissue 112 of the living body to which the contact member 102 is applied and/or to match and/or correspond with the conductivity of one or several other tissues of the living body. In some embodiments, the contact member 102 can comprise a conductive gel such as, for example, a gel containing an electrolyte and/or ions, and can include, for example, a hydrogel, an organogel, or the like. In some embodiments, the contact member 102 can comprise an organic material such as, for example, compressed and/or condensed fat, muscle, skin, including leather, or the like.

The contact member 102 can have a contact surface 103 that is configured to contact tissue 112 and/or be placed proximate to tissue 112, and an opposing back surface 104 that can be configured to be placed relatively less proximate to tissue 112 than contact surface 103. The contact surface 103 and the back surface 104 can be separated by a first distance 105, which first distance 105 is the thickness of the contact member 102. In some embodiments, the first distance 105 can be such that all or desired portions of the electrodes 106 are enclosed and/or contained within the contact member 102.

The treatment device 100 can, as indicated above, include the electrodes 106 which can include the anode 106-A and the cathode 106-B. The electrodes 106 can comprise elongate members that can be electrically connected with the contact member 102. In some embodiments, the electrodes 106 can comprise one or several needles, that can be, for example, length adjustable. In some embodiments, the electrodes 106 can be rigid or flexible, and in some embodiments, the electrodes can be straight, non-straight, and/or curved. The electrodes 106 can have a proximal end 108, a distal end 110, and a longitudinal axis 109 extending therebetween. The electrodes 106 can connect to the contact member 102 in a variety of ways and in a variety of orientations. In some embodiments, and as depicted in FIG. 1, the electrodes 106 can be oriented with respect to the contact member 102 such that the longitudinal axis 109 of the electrodes 106 extends approximately perpendicularly to the contact surface 103 of the contact member 102, and in other embodiments, the electrodes can be oriented with respect to the contact member 102 such that the longitudinal axis 109 of the electrodes 106 extends non-perpendicularly to the contact surface 103 of the contact member 102.

The electrodes 106 can be positioned within the contact member 102 and/or connect with the contact member 102 such that the electrodes are separated by a second distance 114. In some embodiments, the electrodes can be parallel and/or approximately parallel and the second distance 114 can be the same along the length of the electrodes 106. Alternatively, in some embodiments, the electrodes 106 can be non-parallel and the second distance 114 can vary along the length of the electrodes 106.

In some embodiments, the second distance 114 can be determined based on one or several properties of the treatment device 100 and a therewith connected treatment controller. In some embodiments, for example, the treatment controller can generate one or several electrical pulses which result in the generation of the electrical field at the treatment devices 100 that ablates the cancer cells. In such an embodiment, the second distance 114 can be selected based on the properties of these one or several electrical pulses, on the desired properties of the generated electrical field, and/or on the desired treatment outcome. In some embodiments, the second distance 114 can be approximately 0.1 cm, 0.2 cm, 0.3 cm, 0.5 cm, 0.7 cm, 1.0 cm, 1.5 cm, 2.0 cm, 2.5 cm, 3.0 cm, 4.0 cm, 5 cm, 6.5 cm, 8 cm, 10 cm, and/or any other or intermediate value.

In the embodiment depicted in FIG. 1, leads 116, including a first lead 116-A and a second lead 116-B, connect to the proximal ends 108 of the electrodes 106. The leads 116 can be configured to connect the electrodes 106 to the treatment controller and to conduct the one or several electrical pulses from the treatment controller to the treatment device 100, and particularly to the electrodes 106 of the treatment device 100.

In some embodiments, the treatment device 100 can include one or several marking elements 118. The one or several marking elements 118 can be configured to leave a visible mark on tissue 112 that has been contacted by the treatment device 100 and/or that has been treated by the treatment device 100. The marking element 118 can mark the tissue 112 in any desired manner and can, in some embodiments, apply a biocompatible dye and/or ink to the tissue 112, can sear the tissue 112, or the like. Advantageously, the marking element 118 can allow the improved treatment of the tissue by indicating which tissue 112 is treated and which tissue 112 is untreated.

Figure 2:
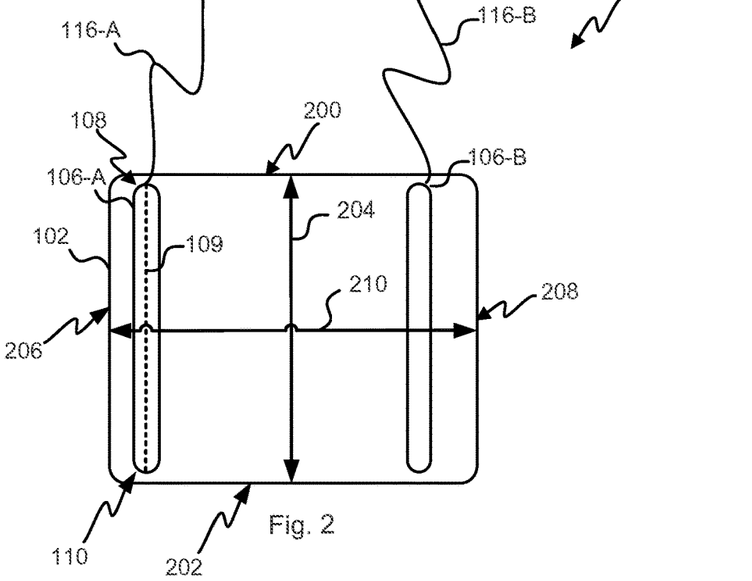
FIG. 2 is a top view of one embodiment of a treatment device having electrodes parallel to a contact surface.

With reference now to FIG. 2, a top view of one embodiment of the treatment device 100 is shown. As seen, the treatment device 100 includes a rectangular contact member 102 connected to electrodes 106, and specifically to the anode 106-A and the cathode 106-B. In contrast to the embodiment of FIG. 1 in which the longitudinal axis 109 of the electrodes 106 are perpendicular to the contact surface 103, the longitudinal axis 109 of the electrodes 106 are non-perpendicular to the contact surface, and specifically are approximately parallel with the contact surface 103 of the contact member 102.

The contact member 102 includes a front 200 positioned adjacent to the proximate end 108 of the electrodes 106 and an opposing back 202 positioned adjacent to the distal ends 110 of the electrodes 106. The front 200 and the back 202 are separated by a lengths 204 of the contact member 102. In some embodiments, the length 204 can be such that all or portions of the electrodes 106 are contained within the contact member.

As seen in FIG. 2, the contact member 102 includes a first side 206 and a second side 208 that are separated by the width 210 of the contact member 102. In some embodiments, the width 210 of the contact member 102 can be such that the electrodes 106 can be spaced with a desired second distance 114.

Figure 3:
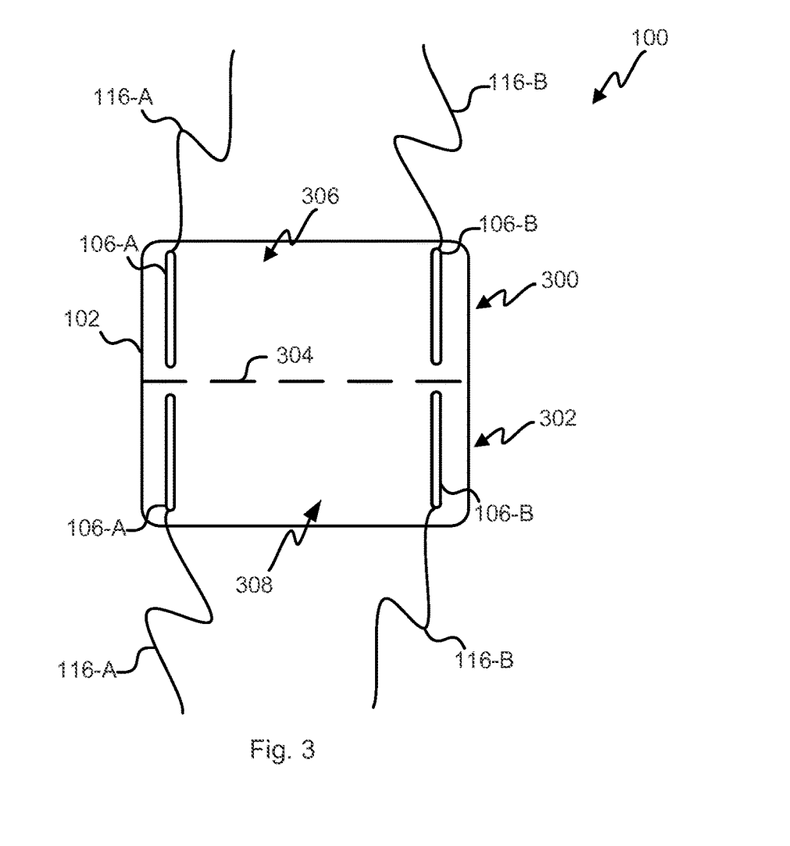
FIG. 3 is a top view of one embodiment of a hinged treatment device.

With reference now to FIG. 3, a top view of one embodiment of the treatment device 100 is shown. As seen, the treatment device 100 includes a rectangular contact member 102 connected to electrodes 106, and specifically to the anode 106-A and the cathode 106-B. The embodiment of the treatment device 100 shown in FIG. 3 includes a contact member 102 having a first portion 300 and a second portion 302 that are connected by hinge 304. In some embodiments, all or portions of the contact member may be flexible and/or rigid. In embodiments in which all or portions of the contact member 102 are rigid, the contact member 102 can be divided into the first and second portions 300, 302 that are connected by hinge 304 to allow some degree of conformity of the contact member 102 to the tissue 112 to thereby improve the effectiveness of the treatment device 100 in ablating one or several cancer cells. In such an embodiment, the contact member may include a first pair of electrodes 306 including, for example, the anode 106-A and the cathode 106-B, located on the first portion 300, and a second pair of electrodes 308 including, for example, the anode 106-A and the cathode 106-B, located on the second portion 302. Advantageously, location of first and second pairs of electrodes 306, 308 on the first and second portions 300, 302 of the contact member 102 can increase the effectiveness of the treatment device 100.

Figure 4:
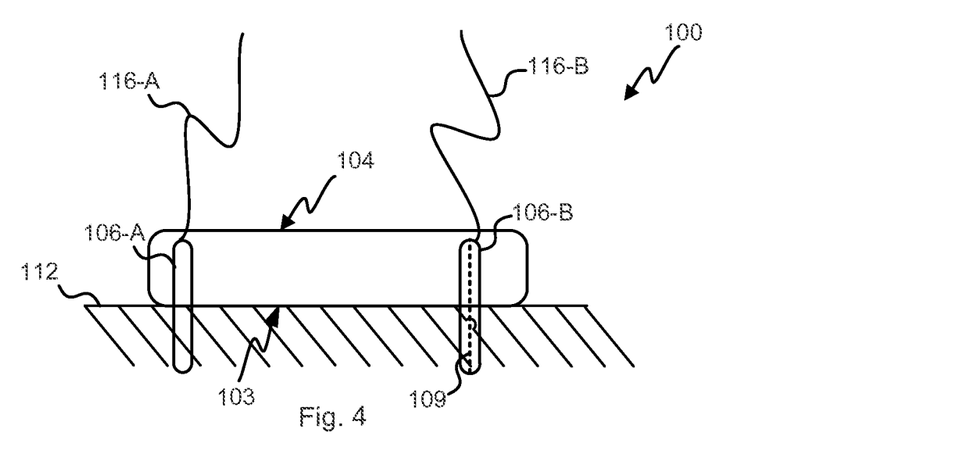
FIG. 4 is a front view of one embodiment of a treatment device having electrodes extending from inside a contact member to outside of the contact member.

With reference now to FIG. 4, a front view of an alternate embodiment of the treatment device 100 is shown. As seen in FIG. 4, the electrodes 106 are positioned such that the longitudinal axis 109 of the electrodes 106 is approximately perpendicular to the contact surface 103 and/or to the back surface 104. As further seen in FIG. 4, the electrodes 106 extend from one side of the contact surface 103 to the other side of the contact surface 103, and specifically extend from an interior portion of the contact member 102 to outside of the contact member 102. Particularly in such an embodiment, one or several voltage-delivery portions of the electrodes may be located either entirely within the contact member 102, entirely outside of the contact member 102, or extending from inside of the contact member 102 to outside of the contact member 102. In some embodiments, such a configuration can be used to allow the insertion of the electrodes 106 into the tissue 112.

Figure 5:
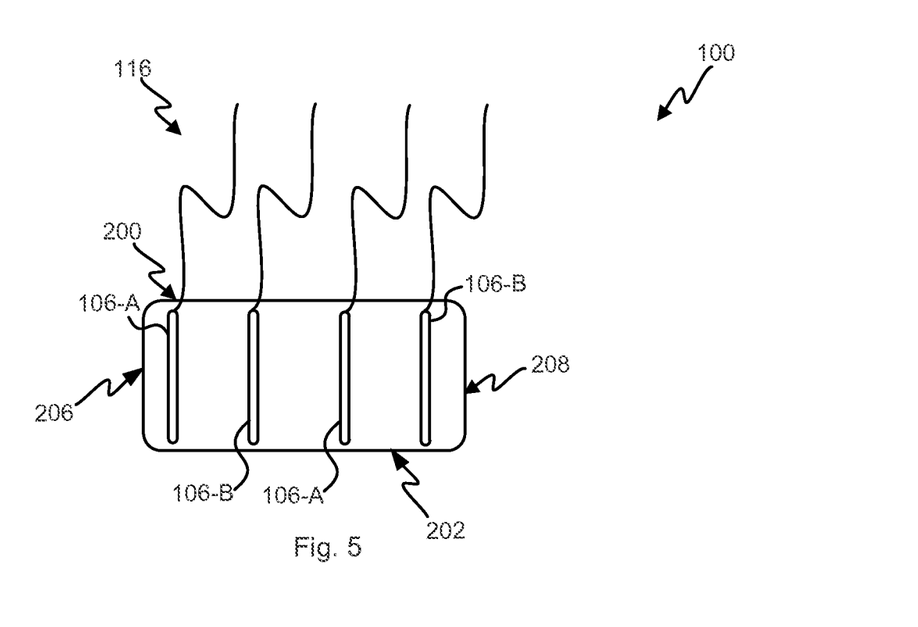
FIG. 5 is a top view of one embodiment of a treatment device having four electrodes.

With reference now to FIG. 5, a top view of an alternate embodiment of the treatment device 100 is shown, which alternate embodiment includes four electrodes 106.

Although specific embodiments disclosed herein depict treatment devices 100 include two or four electrodes 106, the treatment device 100 can include, for example, 2, 3, 4, 5, 6, 7, 8, 9, 10, 15, 20, 30, 50, 100, 500, 1,000, or any other or intermediate number of electrodes 106.

The four electrodes 106 depicted in FIG. 5 include two anodes 106-A and two cathodes 106-B, which are alternatingly positioned such that each of the anodes 106-A is adjacent to one or more of the cathodes 106-B and is not adjacent to the other of the anodes 106-A, and such that each of the cathodes 106-B is adjacent to one or more of the anodes 106-A and is not adjacent to the other of the cathodes 106-B. As seen, the electrodes are positioned such that the longitudinal axes 109 of the electrodes 106 are approximately parallel to the contact surface 103 and/or to the back surface 104.

Figure 6A:
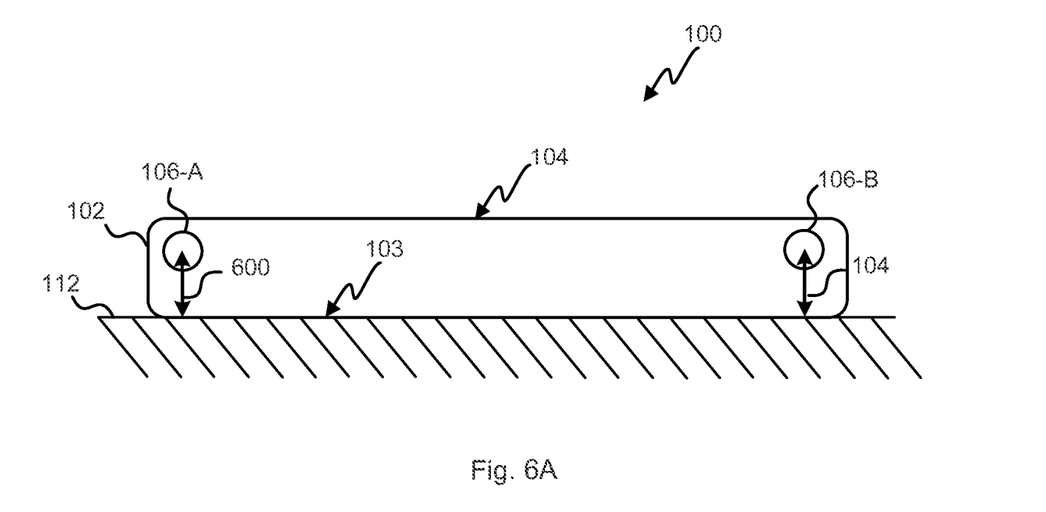
FIG. 6A is a front view of one embodiment of a treatment device showing spacing between portions of the electrodes and the contact surface of the contact member.
Figure 6B:
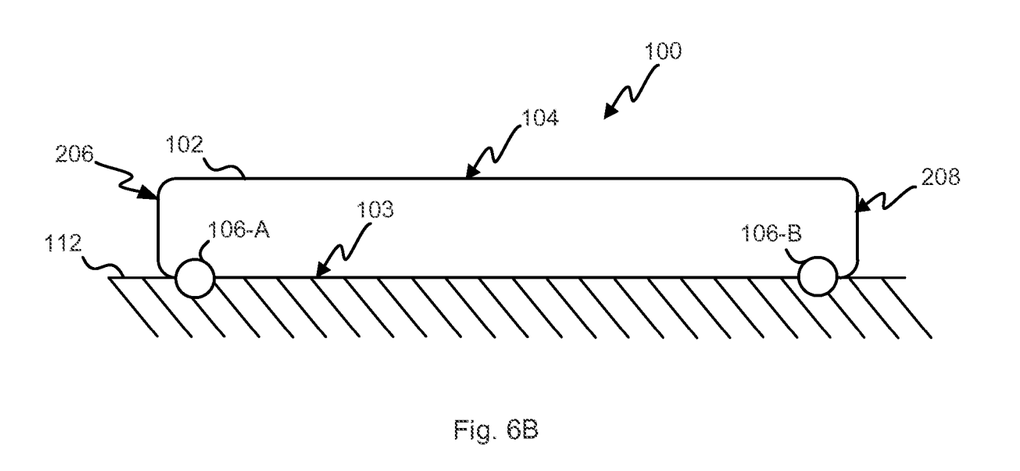
FIG. 6B is a front view of one embodiment of a treatment device in which portions of the electrodes extend to outside of the contact member.

With reference now to FIGS. 6A and 6B, front views of two embodiments of the treatment device 100 are shown. In the embodiments in FIGS. 6A and 6B, the electrodes are positioned such that their longitudinal axes 109 (not visible as the axes extend into the page) are parallel with the contact surface 103 and/or with the back surface 104. These electrodes 106, and specifically the longitudinal axes 109 of these electrodes 106, are spaced from the contact surface by an offset distance 600. As seen in comparing the embodiment of FIGS. 6A and 6B, the offset distance can vary, and in some embodiments, and as shown in FIG. 6B, the offset distance can be zero and/or approximately zero and the longitudinal axes 109 of the electrodes 106 can be positioned on, above, or below the contact surface 103 such that portions of the electrodes 106 extend past the contact surface 103 to outside of the contact portion 102 of the treatment device 100. Advantageously, such positioning can facilitate deeper treatment of the tissue 112 by non-penetratingly deforming tissue 112 proximate to the electrodes 106 such that portions of the tissue 112 are between the electrodes 106.

Figure 7:
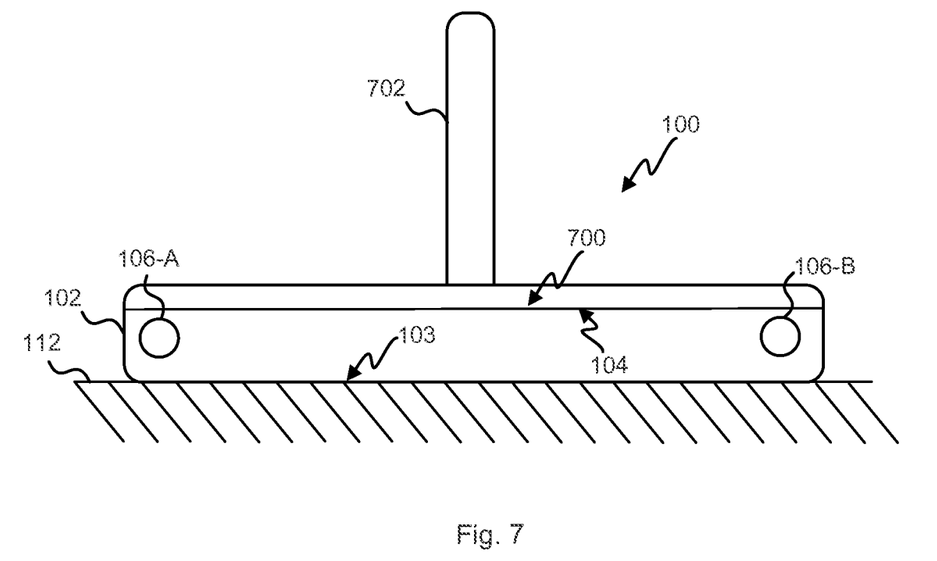
FIG. 7 is a front view of one embodiment of a treatment device having a handle.

With reference now to FIG. 7, a front view of one embodiment of the treatment device 100 positioned on tissue 112 is shown. The treatment device 100 includes contact member 102 having the contact surface 103 and the back surface 104, and electrodes 106 connected to contact member 102. In the embodiment in FIG. 7, a support 700 is attached to the back surface 104 of the contact member 102, which support can increase the rigidity of the contact member 102 and/or provide an interface whereby a handle 702 is connected to contact member 102. In some embodiments in which the support 700 is attached to the back surface 104 of the contact member 102, the rigidity of the support 700 prevents the contact member 102 from bending, and thus rigidifies the contact member 102. In some embodiments, the handle 702, either alone or in combination with the support 700, can facilitate use of the treatment device 100 by enabling a user to easily grip and manipulate the treatment device. The support 700 and the handle 702 can comprise a variety of shapes and sizes and can be made from a variety of materials.

Figure 8:
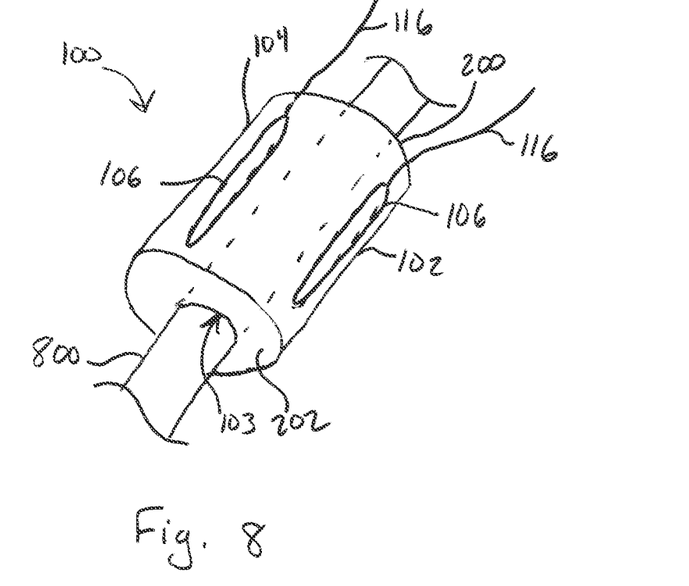
FIG. 8 is a perspective view of one embodiment of a treatment device wrapped around tissue.

With reference now to FIG. 8, a perspective view of one embodiment of a wrapped application of the treatment device 100 is shown. In this embodiment, the contact member 102 of the treatment device 100 is wrapped around tissue 800, which tissue 800 can be, for example, all or a portion of an artery, a blood vessel, a nerve, an organ, or the like. As seen in FIG. 8, the wrapping of the contact member 102 around the tissue 800 can position the electrodes 106 around the periphery of the tissue 800.

Figure 9:
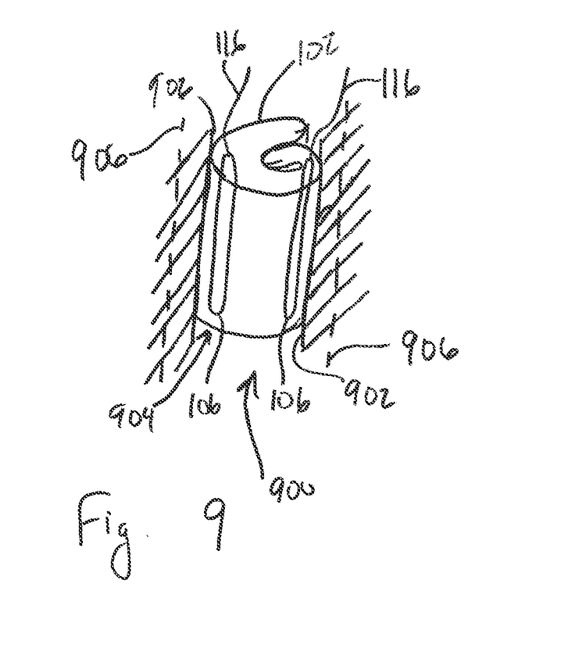
FIG. 9 is a perspective view of one embodiment of a treatment device rolled into a cylinder and inserted into a void.

With reference now to FIG. 9, a perspective view of one embodiment of an inserted application of the treatment device 100 is shown. In this embodiment, the treatment device 100 is inserted into a void 900 defined by tissue that forms tissue walls 902. In some embodiments, the void 900 can be naturally occurring in the body such as, for example, in the throat, in the mouth, in a sinus, in a nasal passageway, in the esophagus, in the trachea, in the vagina, in the colon, in the rectum, or the like, and in some embodiments, the void 900 can be created as part of a treatment.

In some embodiments, the treatment device 100 can be sized and shaped to fill the void 900. In the embodiment of FIG. 9, the contact member 102 of the treatment device 100 is rolled to create a cylindrical insert 904 that is then inserted into the void 900.

In some embodiments, and as is the case in the embodiment of FIG. 8, the treatment device 100 ablates one or several cancer cells located between the electrodes 106. However, in some embodiments, the treatment device can ablate one or several cancer cells that are not located between the electrodes 106, but that are sufficiently proximate to the electrodes 106, to an electrode pair, and/or to the contact member 102. In some embodiments, one or several cancer cells can be ablated when they are within 0.1 cm, 0.2 cm, 0.3 cm, 0.5 cm, 0.75 cm. 1.0 cm, 1.5 cm, 2.0 cm, 2.5 cm, 3.0 cm, 5 cm, and/or any other or intermediate distance from one of the electrodes, from an electrode pair, and/or from the contact member 102. This distance is depicted in FIG. 9 by dashed lines 906.

Figure 10:
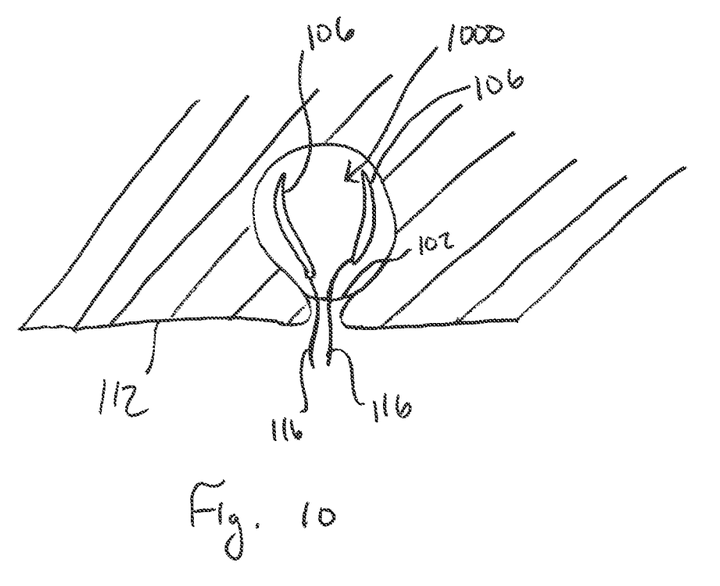
FIG. 10 is a section view of one embodiment of a treatment device in a void.

With reference now to FIG. 10, a section view of one embodiment of a filled application of the treatment device 100 is shown. In this embodiment, the treatment device can be inserted into a void 1000 created by the excision of tissue. In one particular embodiment, two or more electrodes 106 can be inserted into the void 1000 and material for forming the contact member 102 can be filled into the void and can connect with the two or more electrodes 106.

Figure 11:
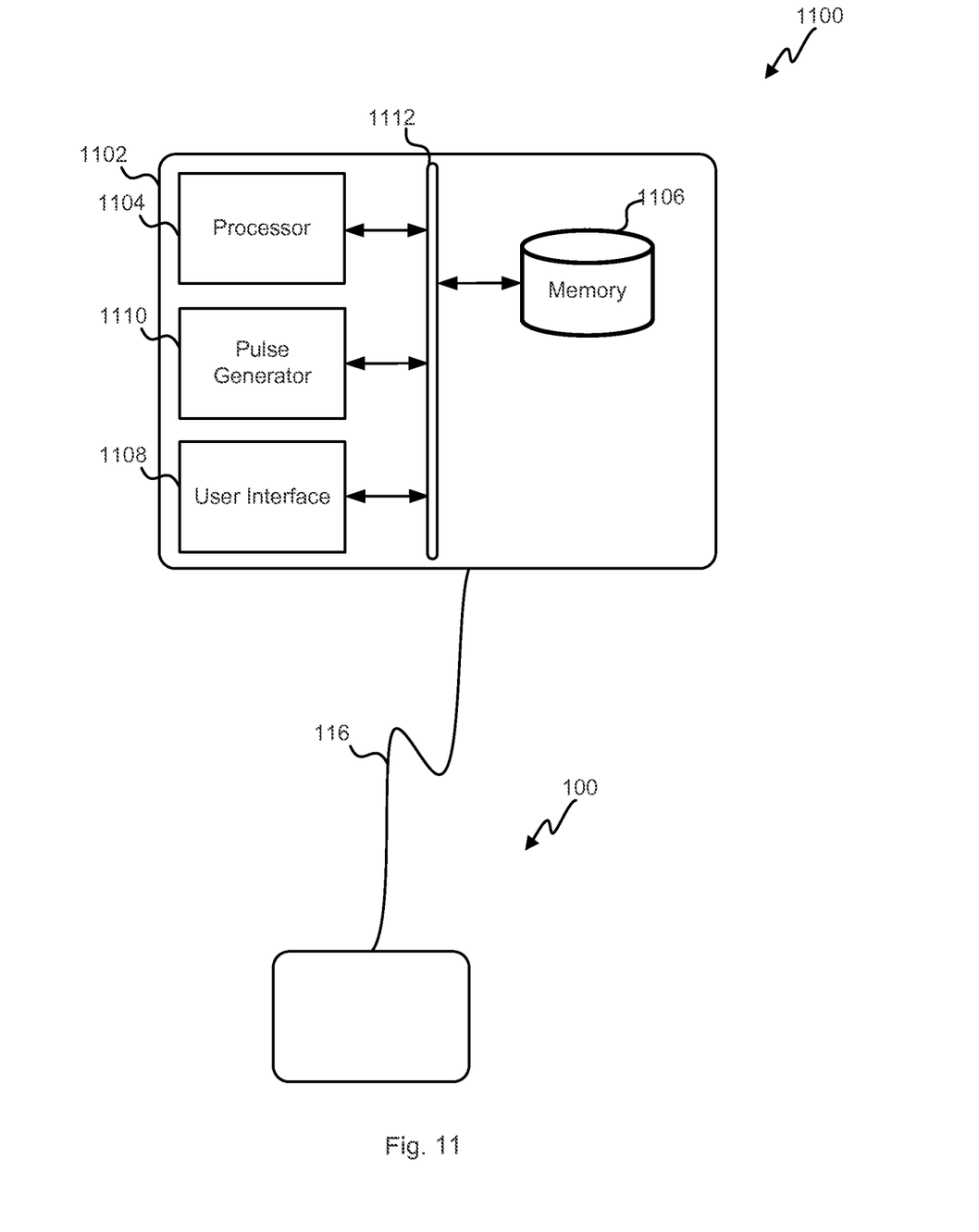
FIG. 11 is a schematic illustration of one embodiment of a treatment system.

With reference now to FIG. 11, a schematic illustration of one embodiment of a treatment system 1100 is shown. The treatment system 1100 can include the treatment device 100 and a treatment controller 1102. As seen in FIG. 11, the treatment device 100 can connect to the treatment controller 1102 via lead 116. The treatment controller 1102 can be configured to control the treatment, and specifically, the treatment controller 1102 can generate one or several electrical pulses of one or several frequencies and/or strengths to ablate one or several cells, including cancer cells that are proximate to the treatment device 100.

The treatment controller 1102 can include a processor 1104. The processor 1104 can be configured to receive information, in the form of electronic signals from one or several of the components of the treatment system 1100 and specifically from the components of the treatment controller 1102, and to send control instructions to one or several of the components of the treatment system 1100 and specifically to the components of the treatment controller 1102. The processor 1104 can act according to stored instructions, which stored instructions can be located in memory associated with the processor and/or in other components of the treatment system 1100 and/or of the treatment controller 1102. The processor 1104 can be a microprocessor, such as a microprocessor from Intel® or Advanced Micro Devices, Inc.®, or the like.

The treatment controller 1102 can include memory 1106. The memory 1106 can be volatile memory or non-volatile memory. The memory 1106 can be RAM memory, flash memory, ROM memory, EPROM memory, EEPROM memory, registers, hard disk, a removable disk, a CD-ROM, or any other form of storage medium known in the art. The memory 1106 can be a component of the processor 1104, associated with the processor 1104, and/or separate from the processor 1104.

The treatment controller 1102 can include a user interface. The user interface 1102 can include a screen having one or several pixels, a speaker, a monitor, a keyboard, a microphone, a mouse, a touchpad, a keypad, or any other feature or features that can receive inputs from a user and provide information to a user. In some embodiments, the user interface 1102 can allow the user to provide one or several inputs to the treatment controller 1102.

The treatment controller 1102 can include a pulse generator 1110. The pulse generator 1110 can be configured to generate the one or several electrical pulses that lead the ablation of the one or several cells, which cells can include one or several cancer cells. The pulse generator 1110 can be configured to selectably alter aspects of the electrical pulses such as, for example, the frequency of the electrical pulses, the duration of the electrical pulses, the strength of the electrical pulses, the voltage of the electrical pulses, or any other desired aspect of the electrical pulses.

The components of the treatment controller 1102 can be communicatingly linked. In the embodiment depicted in FIG. 11, the components of the treatment controller 1102 are communicatingly linked via BUS 1112, however any desired wire or wireless connection between the components may be used.

Figure 12:
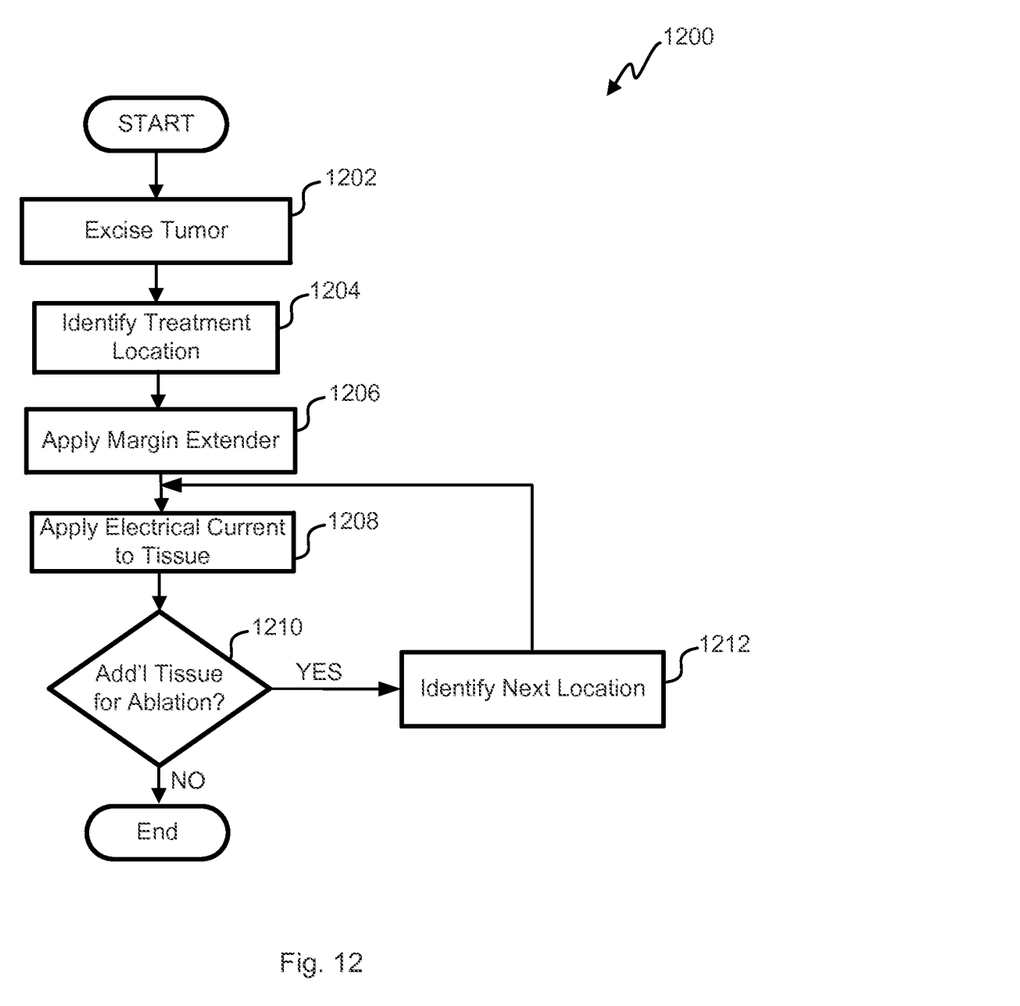
FIG. 12 is a flowchart illustrating one embodiment of a process for ablating a cancer cell.

With reference now to FIG. 12, a flowchart illustrating one embodiment of a process 1200 for ablating a cancer cell is shown. The process 1200 begins at block 1202 wherein a tumor is excised. In some embodiments, this step can include, for example, identifying the location of the tumor and/or of one or several cancer cells, identifying the tumor and/or one or several cancer cells, determining to remove the tumor, accessing the tumor via one or several incisions, and removing the tumor.

After the tumor has been excised, the process 1200 proceeds to block 1204, wherein the location of desired ablation is identified. In some embodiments, this can include determining where and how to place the margin extender 100. This determination can be based on the type of margins achieved with the excision of the tumor, based on the identification of the location of one or several tumors, cancer cells, and/or suspected cancer cells, and/or on all tissue surrounding the location from which the tumor was excised.

After the ablation location has been identified, the process 1200 proceeds to block 1206, wherein the margin extender 100 is applied to tissue. In some embodiments, this step can include the assembly of the margin extender 100 from a kit containing one or several electrodes 106, the contact member 102, and leads 116. The margin extender can be assembled by inserting the one or several electrodes into the contact portion 102 and/or trimming the contact portion 102 to a desired size.

Returning again to the application of the margin extender 100 to tissue, in some embodiments, the tissue to which the treatment device 100 is applied can be proximate to the location from which the tumor was excised, can be proximate to a non-excised tumor, can be proximate to one or several cancer cells, and/or can be proximate to one or several suspected cancer cells. In some embodiments, the application of the margin extender 100 can include placing the margin extender 100 on the tissue, wrapping the margin extender 100 around some or all of the tissue, and/or filling a void with the margin extender 100. In some embodiments, this can be performed as discussed above.

After the margin extender 100 has been applied, the process 1200 proceeds to block 1208 wherein an electrical current is applied to the tissue. In some embodiments, this electrical current can be generated by the treatment controller 1102 according to one or several user inputs received at the treatment controller. These electrical currents and/or electrical fields can be applied to the tissue via the treatment device 100. After the electrical current and/or field has been applied, the process 1200 proceeds to decision state 1210, wherein it is determined if additional tissue should be ablated. In some embodiments, this can include determining whether all of the desired ablation has been performed.

If it is determined that additional tissue should be ablated, then the process 1200 proceeds to block 1212, wherein the next ablation location is identified, after which the process 1200 returns to block 1208 and proceeds as outlined above. If it is determined that no additional ablation is desired, then the process 1200 can, in some embodiments, terminate.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A surgical margin extender comprising:
an anode;
a cathode; and
a contact member, wherein the contact member comprises a conductive material, wherein the contact member electrically connects the anode and the cathode; and wherein the contact member electrically connects the anode and cathode at a distance such that the anode and the cathode can electroporate a cancer cell, wherein the contact member is a planar structure that forms a cylindrical insert by rolling a first end region of the contact member to overlap a second end region of the contact member.

2. The margin extender of claim 1, wherein the anode comprises a first elongate member and wherein the cathode comprises a second elongate member.

3. The margin extender of claim 2, wherein the first elongate member comprises a first needle having a first proximal end and a first distal end, and wherein the second elongate member comprises a second needle having a second proximal end and a second distal end.

4. The margin extender of claim 2, wherein the first elongate member and the second elongate member are parallel when connected to the contact member.

5. The margin extender of claim 4, wherein the first elongate member comprises a first voltage-delivery portion and a first insulative portion, and wherein the second elongate member comprises a second voltage-delivery portion and a second insulative portion.

6. The margin extender of claim 5, wherein the first and second voltage-delivery portions of the first and second elongate members are at least partially connected to the contact member.

7. The margin extender of claim 6, wherein the first and second voltage-delivery portions of the first and second elongate members are completely connected to the contact member.

8. The margin extender of claim 6, wherein the contact member comprises a contact surface configured for connecting with a living tissue.

9. The margin extender of claim 8, wherein the first and second voltage-delivery portions of the first and second elongate members extend from within the contact member to beyond the contact surface of the contact member.

10. The margin extender of claim 1, wherein the contact member is flexible.

11. The margin extender of claim 1, further comprising a handle extending from the contact member, wherein the handle is configured to allow gripping of the treatment device.

12. The margin extender of claim 1, wherein the first end region forms a first edge of the contact member and the second end region forms a second, opposed edge of the contact member.

13. The margin extender of claim 12, wherein the first end region and the second end region are in juxtaposed contact with one another.

14. A treatment system comprising:
a control module, wherein the control module is configured to generate at least one electrical pulse configured to electroporate a cancer cell;
a surgical margin extender comprising:
an anode;
a cathode; and
a contact member electrically connecting the anode and cathode in a configuration such that the anode and the cathode can electroporate the cancer cell via the transmission of the at least one pulse to a living tissue, wherein the contact member is a planar structure that forms a cylindrical insert by rolling a first end region of the contact member to overlap a second end region of the contact member; and
leads connecting the anode and the cathode to the control module.

15. The treatment system of claim 14, wherein the anode comprises a first elongate member and wherein the cathode comprises a second elongate member.

16. The treatment system of claim 15, wherein the first elongate member and the second elongate member are parallel when connected to the contact member.

17. The treatment system of claim 16, wherein the contact member comprises a contact surface configured for electrically connecting with a living tissue.

18. The treatment system of claim 17, wherein the first and second elongate members are parallel with the contact surface.

19. The treatment system of claim 17, wherein the first and second elongate members intersect the contact surface.

20. The treatment system of claim 19, wherein the first and second elongate members extend from one side of the contact surface to the other side of the contact surface.

21. The treatment system of claim 14, wherein the contact member is flexible.

22. The treatment system of claim 14, further comprising a handle extending from the contact member, wherein the handle is configured to allow gripping of the treatment.

23. The treatment system of claim 14, wherein the first end region forms a first edge of the contact member and the second end region forms a second, opposed edge of the contact member.

24. The treatment system of claim 23, wherein the first end region and the second end region are in juxtaposed contact with one another.

25. A method of treating a cancer, the method comprising:
identifying the location for providing a treatment;
applying a surgical margin extender to tissue at the treatment location, wherein the margin extender comprises:
an anode;
a cathode; and
a contact member, wherein the contact member comprises a conductive material that electrically connects the anode and the cathode; and wherein the contact member electrically connects the anode and cathode at a distance such that the anode and the cathode can electroporate the cancer cell;
rolling the contact member to form a cylindrical insert and inserting the cylindrical insert into a void defined by the tissue, wherein the contact member has a first end region and an opposed second end region, and wherein the first end region overlaps the second end region;
applying an electrical current to the contact member via the anode and cathode, wherein the application of the electrical current to the contact member via the anode and the cathode electroporates a cancer cell at the treatment location.

26. The method of claim 25, wherein the tissue proximate to the cancer cell is located on an exterior portion of the body.

27. The method of claim 25, wherein the tissue proximate to the cancer cell is located on an interior portion of the body.

28. The method of claim 27, wherein the interior portion of the body is accessible via an existing orifice.

29. The method of claim 28, wherein the interior portion of the body comprises at least one of:
a nasal passageway;
a mouth;
a throat;
an esophagus;
a trachea;
a vagina;
a rectum; and
a colon.

* * * * *